(12) United States Patent
Svanberg et al.

(10) Patent No.: US 8,067,244 B2
(45) Date of Patent: Nov. 29, 2011

(54) METHOD AND DEVICE FOR INVESTIGATION OF A SURFACE LAYER

(75) Inventors: Sune Svanberg, Lund (SE); Mikael Sjoholm, Lammhult (SE); Gabriel Somes-Falean, Lund (SE)

(73) Assignee: GasPorOx AB, Dalby (SE)

( * ) Notice: Subject to any disclaimer, the term of this patent is extended or adjusted under 35 U.S.C. 154(b) by 1148 days.

(21) Appl. No.: 10/979,082

(22) Filed: Nov. 2, 2004

(65) Prior Publication Data
US 2005/0148092 A1 Jul. 7, 2005

(51) Int. Cl.
*G01N 21/00* (2006.01)
(52) U.S. Cl. .......................... 436/164; 436/167; 436/170
(58) Field of Classification Search .................. None
See application file for complete search history.

(56) References Cited

OTHER PUBLICATIONS

M. Sjoholm, Analysis of Gas Dispersed in Scattering Media, Optics Letters, Jan. 1, 2001, vol. 26, No. 1, pp. 16-18,, Lund, Sweden.
Joachim Seltman, Indication of slope-grain and biodegradation in wood with electromagnetic waves, Seminar on Scanning Technology and Image . . . ,Sep. 1, 1992, Stockholm, Sweden.

*Primary Examiner* — Yelena G Gakh
*Assistant Examiner* — Robert Xu
(74) *Attorney, Agent, or Firm* — Inskeep IP Group, Inc.

(57) ABSTRACT

A method and device for investigation of a surface layer of a material. The material without surface layer is exposed for a gas and the penetration of the gas into the material is measured. Then the surface layer is applied to the material. Finally, the material including the surface layer is exposed for the gas and the penetration of the gas into the material through the surface layer is measured. The measurement of the passage of the gas into the material is performed by a method comprising measurement of light absorption by the gas by absorption spectroscopy.

10 Claims, 1 Drawing Sheet

METHOD AND DEVICE FOR INVESTIGATION OF A SURFACE LAYER

AREA OF INVENTION

The present invention relates to a method and a device for investigation of a surface layer and the ability of the surface layer to withstand penetration of gas, vapour and liquid. More specifically, laser light is injected into the material and the scattered light is monitored by a spectrometer to determine small but, sharp absorptive features of the gas, such as oxygen. By monitoring free gas in the material and the exchange of the gas with the surrounding atmosphere, gas transport through the surface layer may be monitored.

BACKGROUND OF INVENTION

Gases and liquids may be exchanged between a porous material and the surrounding atmosphere. Different types of sealing techniques or surface layers may be used for influencing the exchange of gas. Surface layers may also have other functions, such as protecting the material from disintegration and/or corrosion and for giving it an esthetically pleasing appearance.

Different types of surface layers may be used, such as paints or plastic films. Paints may be applied to wood surfaces and to different fibre based or synthetic construction materials. Plastic films may be used for packaging products that are to be protected from diffusion of oxygen, nitrogen or water, such as meat products, beverages, vegetables, etc. The object may be to prevent oxygen of the air from reaching the product or the material, or water or water vapour from penetration the material.

Handling of moisture in the construction of buildings may be a problem. Moreover, enclosed gases may be prevented from diffusion, such as for retaining the moisture and preventing drying.

Thus, there is a need for being able to determine the penetration properties of gases and liquids through surface layers for analysis and for the development of better properties of such surface layers.

A method of measuring properties of a material, such as gas contents, is presented in a publication by M. Sjöholm, G. Somesfalean, J. Alnis, S. Andersson-Engels, S. Svanberg: "Analysis of gas dispersed in scattering media", Optics Letters Vol. 26, No. 1, Jan. 1, 2001, pages 16-18. It is mentioned that it would be possible by the technique disclosed therein to monitor in situ physiological and degradation processes in various biological substances. Moreover, dynamic processes may be monitored. Successive gas penetration into an object may be studied.

The method described in said publication is called the GASMAS (GAs in Scattering Media Absorption Spectroscopy) method and permits analysis of free gas in porous media. The important aspect is that the gas has extremely sharp absorption maximum compared to the surrounding material. By means of a narrow band laser and signal enhancement modulation techniques, enclosed gas penetrated by the input light can be monitored and appears as characteristic signals in the diffuse scattered light leaving the material. A demonstrated application is for ordinary oxygen which has been shown to appear in for example wood, frigolite and fruits.

Related technologies are described in EP-0768525 and U.S. Pat. No. 4,676,642.

SUMMARY OF THE INVENTION

The present invention relates to the application of the method for examination of transport processes through surface layers such as paint layers and other surface layers, plastic films etc. In the publication mentioned above, it is described that a material may first be exposed to a gas environment, for example pure nitrogen gas during a few hours. Then, the material is exposed to air oxygen and the successive penetration of oxygen is measured, resulting in the determination of a time constant depending on the permeability of the material. Thus, the speed by which the oxygen of the air penetrates and reoccupies the material is observed. Of a very large technical and practical interest is how a surface barrier influence upon such processes.

The gas permeability of a surface layer may be examined in the following way. The material to be protected is firstly placed in nitrogen gas environment for a first time period. Then, the material is exposed to air and the oxygen gas penetration when the air reoccupies the material is measured with the GASMAS method, resulting in that the time constant is determined. Then, the material is covered by its surface layer while in the nitrogen gas atmosphere, whereupon the material is removed and a new GASMAS measurement during air exposure is performed. A new and longer time constant is determined. By comparing the two time constants determined, the influence of the surface layer may be examined.

The surface layer may comprise, but is not limited to, paints, varnishes, impregnation agents, and protection layers.

Sometimes, the purpose of the surface layer is to allow gases to penetrate to avoid moisture build-up in building materials, such as concrete, and buildings.

In wood, furniture and paper industry, it is of interest to determine the moisture contents before surface treatment, such as varnishing, painting, printing, sheet lamination etc. The new method may be used to characterize these processes.

Moreover, the alteration over time of filters and semipermeable surfaces may be studied.

Furthermore, the liquid penetration into a porous material may be monitored and how efficient a surface layer is for preventing this. An important application is the ingression of water in exposed building materials, such as wood, wood chip board and plaster board. In dry condition, the pores are filled with air and a strong oxygen signal is obtained. If water has penetrated the pores instead of air, the air gas signal is decreased and the water contents may be determined. A surface layer may prevent or reduce the water penetration.

Another method is to measure, in a first step, the oxygen signal and then heat the surface to a certain temperature at which the moisture contents of the material is known and in this way determine the moisture contents.

This type of measurement is based on displacement of gas and may also be used without nitrogen gas exposure and may easily be performed with a portable equipment for example at the building site. With a portable equipment, moreover, nitrogen or water may be pressed into the material with a nozzle or gasket applied towards the surface and the diffusion properties or the moisture durability may be monitored at the same time or shortly thereafter.

Drying of material may also be studied, as well as the performance of methods for protecting against drying, for example plastic or paper laminated based enclosures of food. Also successively appearing gas generation in food, such as meat products, may be monitored for quality check. In relation thereto, a differential diagnostic may be performed between necrotic and non-necrotic human tumors within the oncological sector.

The present invention relates to a measurement method as well as an equipment used for that purpose. The equipment may be of the type fixed-sample equipment or handheld portable measurement equipment. Especially in the latter case, it is desirable that the detected light scattered in the material is detected at the same side and close to the point of light injection. A measurement equipment in which light is injected at a spot and the diffusely scattered light in the material is collected in an optical system with a close lateral position and with a ring shaped light collecting structure, furthermore has the advantage that the measurement does not necessarily be limited by the thickness of the present material. A too thick material does not pass any light. The method is based on the fact that the material is not too light absorbing at the laser wavelength chosen for gas detection.

A portable instrument may be handheld and have a pistol like shape, wherein the optical transmitter and the receiver is pressed towards the material that is to be investigated, for example at the building site. An automatic reduction of possible disturbing background light is also obtained in this way. In the case of measurement of moisture at building sites, free water vapour in the pores may be measured with a laser tuned to one of the absorption line of water. As described above, liquid water, which does not have any sharp absorption maximums, may be studied by the displacement of oxygen out of the pores, resulting in a decreased oxygen signal.

Above has been described molecular oxygen gas and water molecules as examples. Other gases may be used, such as carbon dioxide, formaldehyde, and methane. Suitable light sources for GASMAS includes semiconductor lasers and quantum cascade lasers, which are selected for adapting the absorption structure for the actual gas. Thus, for example the lines in the so called A band of oxygen around 760 nm are suitable and agrees with the working area of commercially easily obtainable equipment. Other narrow band light sources may also be used although they do not use the laser principle.

For solving the above mentioned problems, the invention provides a method for investigation of a surface layer of a material, comprising exposing the material without surface layer for a gas and measuring the effect of said gas in the material; exposing the material including the surface layer for said gas and measuring the effect of said gas in the material through the surface layer; wherein the measurement of the passage of said gas in the material is performed by a method comprising measurement of light absorption by said gas by absorption spectroscopy. The measuring of the passage of the gas into the material comprises obtaining a first and a second time constant for the penetration of the gas into the material. The material may be exposed to a second gas for at least partial displacement of said first gas in said material before exposing the material for said first gas and measuring the penetration of the gas into the material. The first gas may be selected from the group comprising: oxygen, methane, formaldehyde, water vapour and carbon dioxide. The second gas may be nitrogen. The surface layer may be selected from the group comprising: paint, varnish, impregnation agent, plastic film and paper laminate. The material may be selected from the group comprising wood, wood particle board, plasterboard, concrete and food. The method of measuring the penetration of said gas into the material might be a GASMAS method comprising absorption spectroscopy measurement of said gas in scattering media.

BRIEF DESCRIPTION OF DRAWINGS

Further objects, features and advantages of the invention will appear from the following detailed description of embodiments with reference to the appended drawings in which.

DETAILED DESCRIPTION OF EMBODIMENTS

Figure 1:
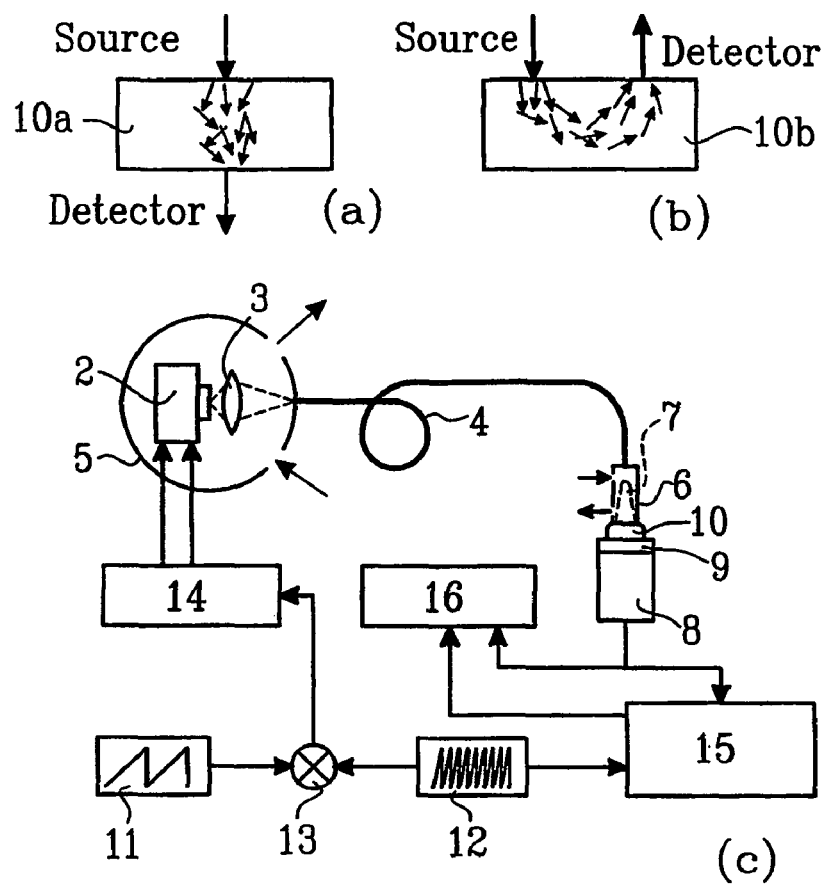
FIG. 1 is a schematic view of a GASMAS equipment intended to be used according to the invention.

FIG. 1 schematically discloses a device 1 for measurement of gas in a scattering medium. A tunable diode laser 2 is used having a nominal wavelength of 757 nm at 25° C. and a free running output power of 7 mW.

The laser is used as a spectroscopic source for molecular oxygen ($O_2$) monitoring. The spectroscopy may be performed on a strong isolated line at 761.003 nm (R7R7). A multitude of lines are available in the oxygen A band and are within the wavelength range of the diode laser used.

Since oxygen is present in normal air, the laser 2 and a lens 3 that focuses the radiation into a 600 µm quartz fibre 4, are arranged in a nitrogen-flushed chamber 5 to eliminate spurious oxygen signals. Alternatively, the fibres may be attached directly to the laser, eliminating the need for nitrogen flushing.

At the other end of the fibre, the output light is collimated by a second lens 6 fixed in a nitrogen-flushed adapter chamber 7. Since the transmitted light intensities through the samples are usually very low, it is important to ensure a high detection sensitivity. Thus, a photomultiplier tube 8 with a 50 mm diameter photocathode is used for detection. The ambient room light is effectively suppressed by a Schott RG695 colored-glass long-pass filter 9 attached directly to the photocathode in combination with the sensitivity fall-off of the photomultiplier tube toward longer wavelengths.

The material 10 is placed directly between the filter 9 and the collimating lens 6, which could be freely positioned by a fine translation stage. The diode laser is operated in a thermoelectrically cooled mount and is current (I) and temperature (T) controlled by a precision diode laser driver 14. Wavelength scanning is achieved by repetitive application of a current ramp obtained by a current ramp generator 11 with a repetition rate of 4 Hz to the drive current, whereas a sinusoidal current at 55 kHz is superimposed for wavelength modulation of the diode laser by a function generator 12. The signals are combined in an adder circuit 13 and provided to the laser driver 14. The photomultiplier tube signal is picked up phase-sensitively by a lock-in amplifier 15. The extracted second-harmonic component and the direct signal are accumulated for 256 scans in a digital oscilloscope 16.

In FIG. 1a, the laser light passes through the material 10a from one side to the other. In FIG. 1b, the light passes into the material 10b and out of the material at the same side, since the material is scattered by the material.

Figure 2:
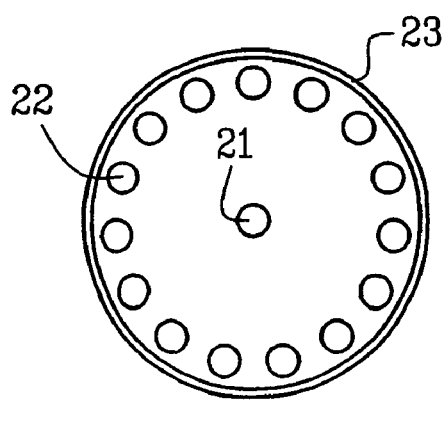
FIG. 2 is a schematic cross-sectional view of a handheld device according to the invention.

The light emerging from the material may be collected by light fibres and passed to the photomultiplier or detecting equipment. When the measurement device is a handheld device it may be pressed against the surface wherein both the output light and the received light is transmitted by light fibres. As schematically shown in FIG. 2, such an embodiment may comprise a central light fibre 21 transmitting the output laser light to the material. The light scattered by the material is collected by several light fibres 22 arranged in a ring around the central light fibre 21. In this way, the week signal of the scattered light is collected efficiently. The light fibres are arranged in a housing 23 having circular cross-section. The housing prevents any outside light from reaching the area to be investigated. It may be possible to arrange that the ring fibres input the light and the central light fibre collects the light.

The method of the invention involves exposing the material for an inert gas, such as nitrogen, displacing the air oxygen in the material. Then, the reoccupation of the material with oxygen is measured.

Alternatively, the material may be arranged in the air, and penetration of a gas not normally present in the air is monitored. Such a gas may be methane.

The gas for penetration of the material may alternatively be pure oxygen. Since oxygen is present in air in a ratio of about 20.4%, the exposure of the material to 100% oxygen would result in an increase of the oxygen contents in the pores of the material. Such penetration may be measured. Another gas that may be used is carbon dioxide.

It is not required that the gas, such as nitrogen, completely displaces the oxygen in the material before new exposure for the first gas. The time constant will be the same even if only partial displacement of the oxygen contents has taken place by nitrogen.

Figure 3:
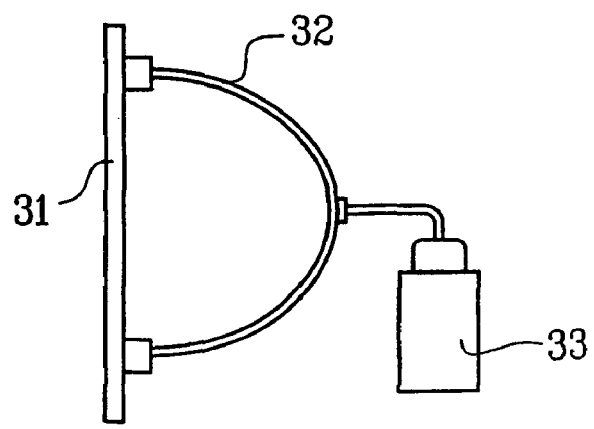
FIG. 3 is a schematic cross-sectional view of a gasket for applying a gas atmosphere to a material.

The exposure of the material to nitrogen may be performed by attaching a gasket 32 of a sufficient size to the material 31 and circulating nitrogen gas of a gas reservoir 33, inside the gasket, for example during four hours, as shown in FIG. 3. Then, the gasket is removed and the penetration of air oxygen is monitored continuously or intermittently. The time constant is determined in a conventional way. The gasket needs to be large enough to cover a sufficient area of the material, so that transport of oxygen from the surrounding material does not disturb or take over the transport of oxygen from the air through the surface layer.

The gasket may be provided with a sealing edge comprising suction means for suction of the gasket towards the surface.

The gasket may as well provide a liquid such as water for penetration of the surface layer and into the pores of the material. Then, the water effect of displacing the oxygen molecules in the material may be monitored.

The method may be performed by firstly exposing the material for a nitrogen atmosphere without surface layer. Such exposure may take place inside a plastic bag or box provided with a nitrogen atmosphere. Another inert gas may as well be used, such as a rare gas, such as helium.

Then, the material is exposed to the air oxygen atmosphere and the displacement of the nitrogen is determined in order to obtain the first time constant.

Then, the surface layer is applied.

Finally the material is exposed to nitrogen atmosphere and the nitrogen displacement of the oxygen is measured, resulting in the second time constant.

It is mentioned that it is not necessary to use the same piece of material. Instead a fist piece of material may be uncovered with the surface layer and another piece of material may be covered and the two pieces of material may be examined simultaneously.

Moreover, the same piece of material may be covered with the surface layer over a part and uncovered over another part, being at a sufficient distance from the first part.

The invention has been described above with reference to embodiments shown on the drawings. However, different features as shown may be combined differently as appears to a skilled person reading this specification. Such and other modifications appearing to a skilled person are intended to be included within the scope of the invention. The invention is only limited by the appended patent claims.

The invention claimed is:

1. A method for determining the influence of a surface layer on the rate with which a gas occupies pores in a material, said method comprising the steps of:
   a) exposing the material without said surface layer to said gas;
   b) measuring light absorption by the gas occupying pores in the material without the surface layer to determine a first time constant for a change in the measured absorption of light by the gas;
   c) exposing the material with the surface layer to said gas;
   d) measuring light absorption by the gas occupying pores in the material through the surface layer to determine a second time constant for a change in the measured absorption of light by the gas; and
   e) comparing the first and second time constants to determine the relative rates with which the gas occupies pores within the material;
   wherein said material is a food and said surface layer is a plastic or paper laminated based enclosure of said food; and,
   wherein the measuring step in b) and/or d) is a GASMAS method comprising absorption spectroscopy measurement of said gas in scattering media.

2. The method of claim 1, wherein the gas is generated in the porous material.

3. The method of claim 1, wherein the porous material is exposed to a liquid or liquid vapor in method steps a) and c) and wherein the first and second time constants measure rates of displacement of the gas from pores in the porous material.

4. A method for determining the influence of a surface layer on the rate with which a gas occupies pores in a material, said method comprising the steps of:
   a) exposing a piece of the material without said surface layer to said gas;
   b) measuring light absorption by the gas occupying pores in said piece of the material without the surface layer to determine a first time constant for a change in the measured absorption of light by the gas;
   c) exposing said piece of the material with the surface layer to said gas;
   d) measuring light absorption by the gas occupying pores in said piece of the material through the surface layer to determine a second time constant for a change in the measured absorption of light by the gas; and
   e) comparing the first and second time constants to determine the relative rates with which the gas occupies pores within the material;
   wherein said material is a food and said surface layer is a plastic or paper laminated based enclosure of said food; and,
   wherein the measuring step in b) and/or d) is a GASMAS method comprising absorption spectroscopy measurement of said gas in scattering media.

5. A method for determining the influence of a surface layer on the rate with which a gas occupies pores in a material, said method comprising the steps of:
   a) exposing a first piece of the material without said surface layer to said gas;
   b) measuring light absorption by the gas occupying pores in the first piece of the material without the surface layer to determine a first time constant for a change in the measured absorption of light by the gas;
   c) exposing a second piece of the material with the surface layer to said gas;

d) measuring light absorption by the gas occupying pores in the second piece of the material through the surface layer to determine a second time constant for a change in the measured absorption of light by the gas; and e) comparing the first and second time constants to determine the relative rates with which the gas occupies pores within the material;

wherein said material is a food and said surface layer is a plastic or paper laminated based enclosure of said food and said first and second piece of the material are separate pieces of the material; and, wherein the measuring step in b) and/or d) is a GASMAS method comprising absorption spectroscopy measurement of said gas in scattering media.

6. The method as in claim 1, wherein said material is exposed to a second gas for at least partial displacement of said gas in said material before exposing the material to said gas in steps a) and c).

7. The method as in claim 1, wherein said gas is selected from the group consisting of: oxygen, methane, formaldehyde, water vapour and carbon dioxide.

8. The method as in claim 1, wherein said second gas is nitrogen.

9. The method of claim 1, wherein said first and second time constants are obtained simultaneously.

10. The method of claim 6, comprising heating said surface layer and thereby displacing said gas.

* * * * *